(12) United States Patent
Hong et al.

(10) Patent No.: US 9,820,933 B2
(45) Date of Patent: Nov. 21, 2017

(54) COMPOSITION FOR STIMULATING HAIR GROWTH OR PREVENTING HAIR LOSS WHICH INCLUDES EXTRACT NEURAL STEM CELL AND METHOD FOR PRODUCING SAME

(71) Applicant: Korea University Research and Business Foundation, Seoul (KR)

(72) Inventors: Sunghoi Hong, Seoul (KR); In-Sik Hwang, Seoul (KR); Kyung-A Choi, Gangwon-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/785,255

(22) PCT Filed: Apr. 16, 2014

(86) PCT No.: PCT/KR2014/003324
§ 371 (c)(1),
(2) Date: Oct. 16, 2015

(87) PCT Pub. No.: WO2014/171746
PCT Pub. Date: Oct. 23, 2014

(65) Prior Publication Data
US 2016/0081913 A1 Mar. 24, 2016

(30) Foreign Application Priority Data
Apr. 19, 2013 (KR) ........................ 10-2013-0043706

(51) Int. Cl.
*A61K 35/30* (2015.01)
*A61Q 7/00* (2006.01)
*A61K 8/98* (2006.01)
*C12N 5/0797* (2010.01)

(52) U.S. Cl.
CPC .............. *A61K 8/981* (2013.01); *A61K 35/30* (2013.01); *A61Q 7/00* (2013.01); *C12N 5/0623* (2013.01); *C12N 2501/11* (2013.01); *C12N 2501/115* (2013.01); *C12N 2501/235* (2013.01)

(58) Field of Classification Search
CPC .......... A61K 35/30; A61K 8/981; A61Q 7/00; C12N 5/0623
See application file for complete search history.

(56) References Cited

U.S. PATENT DOCUMENTS

| 5,958,767 | A | * | 9/1999 | Snyder | ................. | C12N 5/0623 |
| | | | | | | 435/368 |
| 6,372,494 | B1 | * | 4/2002 | Naughton | ................ | A61K 8/02 |
| | | | | | | 424/115 |
| 2008/0286243 | A1 | | 11/2008 | Kang et al. | | |
| 2012/0121522 | A1 | * | 5/2012 | Gruber | ..................... | A61K 8/99 |
| | | | | | | 424/59 |

FOREIGN PATENT DOCUMENTS

| KR | 10-0771171 B1 | 10/2007 |
| KR | 10-2008-0097593 A | 11/2008 |
| KR | 10-2010-0097574 A | 9/2010 |
| KR | 10-1026070 B1 | 3/2011 |
| KR | 10-2012-0096185 A | 8/2012 |
| KR | 10-1218101 B1 | 12/2012 |
| KR | 10-2013-0009117 A | 1/2013 |

OTHER PUBLICATIONS

Lim et al, Neurosci. Letters 435:175-180, 2008.*
Flax et al, Nature Biotech. 16:1033-1039, 1998.*
Lu et al, Exp. Neurology 181:115-129, 2003.*
Won et al, J. Dermatol. Sci. 57:132-146, 2010.*
Park et al, Biomed. Res. 31(1):27-34, 2010.*
Schanzer et al, Brain Pathol. 14(3):237-248, 2004; abstract only.*
Chen et al, J. Neurosci. Res. 88:3308-3318, 2010.*
Carpenter et al, Exp. Neurol. 158:265-278, 1999.*
Svendsen et al, J. Neurosci. Methods 85:141-152, 1998.*
Tarasenko et al, J. Neurosci. Res. 78:625-636, 2004.*
Flax, J., et al., "Engraftable human neural stem cells respond to developmental cues, replace neurons, and express foreign genes", "Nature Biotechnology", Nov. 1998, pp. 1033-1039, vol. 16.
Lim, H., et al., "Neuroprotective effect of neural stem cell-conditioned media in in vitro model of Huntingtons disease", "Neuroscience Letters", 2008, pp. 175-180, vol. 435.

* cited by examiner

*Primary Examiner* — Kevin Hill
(74) *Attorney, Agent, or Firm* — Hultquist, PLLC; Steven J. Hultquist (57) ABSTRACT

The present invention relates to a composition for stimulating hair growth or preventing hair loss, which contains a conditioned medium or extract of neural stem cells (NSCs) isolated from the ventricular zone of the human brain, and to a preparation method thereof. The conditioned medium or extract of neural stem cells according to the present invention contains various growth factors and cytokines, and thus has an excellent effect on the stimulation of hair growth. Thus, it is useful for hair growth stimulation and hair loss prevention.

9 Claims, 11 Drawing Sheets

COMPOSITION FOR STIMULATING HAIR GROWTH OR PREVENTING HAIR LOSS WHICH INCLUDES EXTRACT NEURAL STEM CELL AND METHOD FOR PRODUCING SAME

CROSS-REFERENCE TO RELATED APPLICATIONS

This application is a U.S. national phase under the provisions of 35 U.S.C. §371 of International Patent Application No. PCT/KR14/03324 filed Apr. 16, 2014, which in turn claims priority of Korean Patent Application No. 10-2013-0043706 filed Apr. 19, 2013. The disclosures of such international patent application and Korean priority patent application are hereby incorporated herein by reference in their respective entireties, for all purposes.

TECHNICAL FIELD

The present invention relates to a composition for stimulating hair growth or preventing hair loss, which contains an extract of neural stem cells, and a preparation method thereof. More specifically, the present invention relates to the novel use of a conditioned medium of ectodermal neural stem cells or an extract of ectodermal neutral stem cells, and to a composition for stimulating hair growth or preventing hair loss, which contains a conditioned medium or extract of cultured neural stem cells (NSCs) isolated from the ventricular zone of the human brain.

BACKGROUND ART

Hair follows a specific hair cycle. A phase in which keratinocytes around hair dermal papilla divide and proliferate is referred to as "anagen". Anagen is followed by catagen in which hair stops its growth and is separated from the hair papilla. Catagen is followed by telogen in which keratinocytes do not grow and hair is lost after a certain period of time. The hair cycle consists of anagen, catagen and telogen, which are repeated. The anagen phase in adults usually differs between individuals, but it is known that the anagen phase is 3-5 years for males and 4-6 years for females and that about 15% of hair is in the catagen and telogen phases. Human hairs follow independent hair cycles, and grow on one side but are lost on the other side so that the total number of hairs will be uniformly maintained. This hair loss is referred to as physiological hair loss. However, in addition to the telogen phase of the normal hair cycle, diseases, hair care products (gel, wax, etc.), stress and the like may cause hair loss, and in this case, when the cause is removed, the hair growth is restored again.

Baldness does not mean that hair does not grow again after hair loss. In the case of baldness, hair gradually become thinner and converts to vellus hair. As this phenomenon progresses, the hair papilla present in the hair root becomes smaller. When the hair papilla becomes smaller, the thickness of the hair also become thinner and, at the same time, the hair cycle becomes shorter, and newly grown hair becomes further thinner. As baldness continuously progresses, the hair converts to vellus hair, and the hair cycle becomes shorter so that the hair is lost faster than growth. In addition, unlike alopecia areata known to be caused by autoimmune disease, and temporal hair loss that is caused by endocrine disease, nutritional deficiency, drugs, or physical and mental stresses such as child birth, baldness tends to be inherited, and the degree of baldness is diverse. Furthermore, baldness is known to be associated with a blood male hormone (androgen).

Currently, it is known that, when Minoxidil that is a topical medication and Propecia (finasteroid component) that is an oral drug are used in the initial stage of hair loss, the progression of hair loss can be somewhat delayed. However, already progressed hair loss is difficult to restore to the normal state, and in this case, hair transplantation can be considered. In hair transplantation, about 1000-3000 hairs are collected by an incision method or (non-incision method) from side hairs above the ear portion and back hairs, which are less sensitive to hormones, and the collected hairs are transplanted. However, the number of hair transplantations is limited.

Currently commercially available products are known to have effects on the prevention of hair loss, but show insignificant effects on hair growth. In addition, when the use of these products is stopped, problems arise again. Furthermore, these products are disadvantageous in terms of costs.

In recent years, methods of treating hair loss using genes and methods of treating hair loss using stem cells have been developed. In prior art documents related to the background of the present invention, Korean Patent No. 10-0771171 (issued on Oct. 29, 2007) discloses a method comprising isolating and proliferating follicular stem cells and allowing the cells to differentiate into follicular cells, and a composition for treating baldness, and Korean Patent Laid-Open Publication No. 10-2008-0097593 (laid open on Nov. 6, 2008) discloses a cell therapy agent prepared by suitably mixing adipose-derived stem cells with follicular stem cells. In addition, Korean Patent No. 10-1218101 (issued on Jan. 3, 2013) discloses a composition for stimulating hair growth and preventing hair loss, which contains, as an active ingredient, a conditioned medium of amniotic fetal mesenchymal stem cells. However, a composition for stimulating hair growth or preventing hair loss, which contains a conditioned medium of neural stem cells or an extract of neural stem cells and has excellent effects, has not yet been reported.

Accordingly, the present inventors have characterized a conditioned medium of neural stem cells or an extract of neural stem cells by applying the conditioned medium or the extract to human dermal papilla cells (hDPCs), and have found the effects of the conditioned medium or the extract on the stimulation of hair growth or the prevention of hair loss by use of C57BL/6 mice in vivo, thereby completing the present invention.

PRIOR ART LITERATURE

Patent Documents

Patent document 1: Korean Patent No. 10-0771171 (issued on Oct. 29, 2007)
Patent document 2: Korean Patent Laid-Open Publication No. 10-2008-0097593 (laid open on Nov. 6, 2008)
Patent document 3: Korean Patent No. 10-1218101 (registered on Jan. 3, 2013)

DISCLOSURE OF INVENTION

It is an object of the present invention to provide a composition for stimulating hair growth or preventing hair loss, which contains a conditioned medium of neural stem cells or an extract of neural stem cells.

Another object of the present invention is to provide a method of preparing a composition for stimulating hair growth or preventing hair loss, the method comprising using neural stem cells.

These and other objects, features, and advantages of the present invention will become more apparent from the following detailed descriptions, the appended claims, and the accompanying drawings.

BEST MODE FOR CARRYING OUT THE INVENTION

In one aspect, the present invention is directed to a composition for stimulating hair growth or preventing hair loss, which contains a conditioned medium of neural stem cells or an extract of neural stem cells.

In the present invention, the kind of neural stem cells for preparing the composition is not limited. Preferably, the neural stem cells are fetal adult stem cells. In an example of the present invention, neural stem cells isolated from the ventricular zone of the fetal brain were used to prepare a conditioned medium of neural stem cells or an extract of neural stem cells.

As used herein, the phrase "conditioned medium of neural stem cells" refers to a material comprising the components of a conditioned medium obtained by subculturing neural stem cells that are a kind of ectodermal stem cells, and the phrase "extract of neural stem cells" refers to a material comprising cellular components obtained by subculturing neural stem cells that are a kind of ectodermal stem cells, collecting and centrifuging the medium used to culture the neural stem cells, filtering the supernatant, homogenizing the filtrate with a homogenzer to obtain a mixture, and centrifuging the mixture to collect the supernatant (see Example 1).

In the present invention, the extract of neural stem cells may be contained in an amount of 10-30% (v/v), which is an effective concentration that shows no cytotoxicity. Preferably, it may be contained in an amount of 15-25% (v/v). More preferably, it may be contained in an amount of 20% (v/v).

Figure 1:
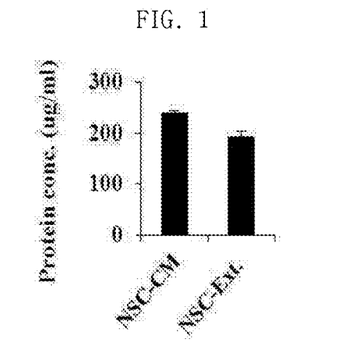
FIG. 1 shows the results of a Brad-ford assay performed to measure the total protein content of each of a conditioned medium of neural stem cells and an extract of neural stem cells according to the present invention.

In an example of the present invention, in order to examine whether the conditioned medium of neural stem cells or the extract of neural stem cells has an activity of stimulating hair growth, the total protein isolated from each of the neural stem cell-conditioned medium (CM) and the neural stem cell extract (Ext.) was assessed by a Bradford assay (FIG. 1).

Figure 2A:
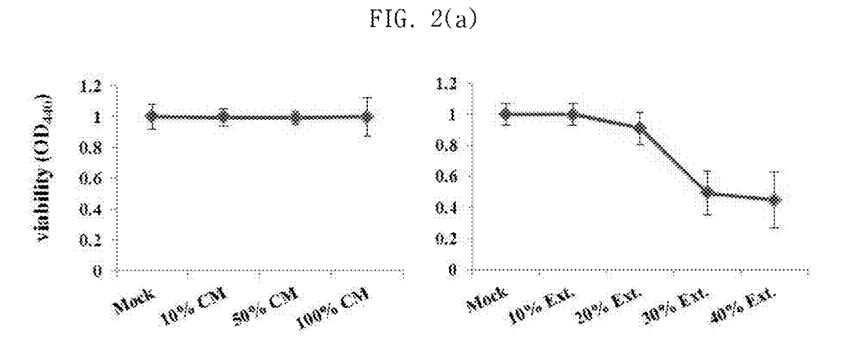
FIGS. 2a and 2b show the results of analyzing the viability and morphology of dermal papilla cells, treated with each of a conditioned medium of neural stem cells and an extract of neural stem cells according to the present invention, by a WST-1 assay and a phase contrast microscope.
Figure 2B:
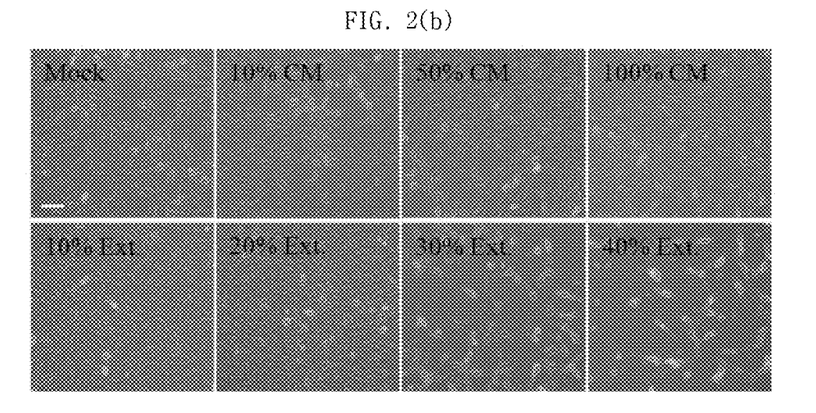

Dermal papilla cells were treated with the conditioned medium of neural stem cells or the extract of neural stem cells according to the present invention for 3 days, after which the viability of the cells was analyzed by a WST-1 assay, and the morphology of the cells was observed with a phase contrast microscope (FIGS. 2a and 2b).

Figure 3:
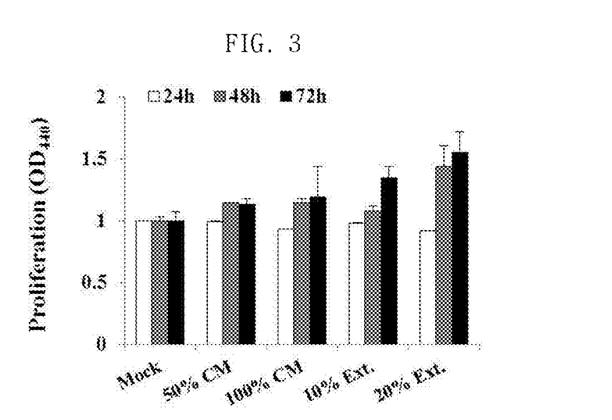
FIG. 3 shows the results of analyzing the proliferation of dermal papilla cells, treated with each of a conditioned medium of neural stem cells and an extract of neural stem cells according to the present invention, by a WST-1 assay.
Figure 4A:
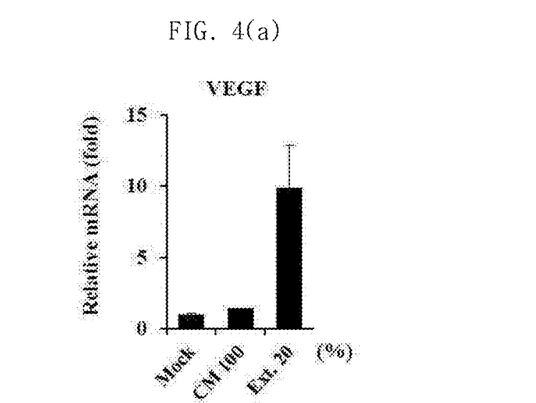
FIGS. 4a to 4e show the results of qRT-PCR and RT-PCR, which indicate that the expression levels of various growth factors and cytokines (Wnt5a, BMP2, TGF-beta2, etc.) in dermal papilla cells were increased when the dermal papilla cells were treated with each of a conditioned medium of neural stem cells and an extract of neural stem cells according to the present invention.
Figure 4B:
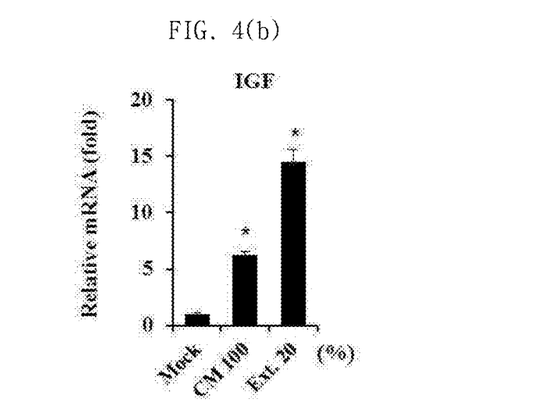
Figure 4C:
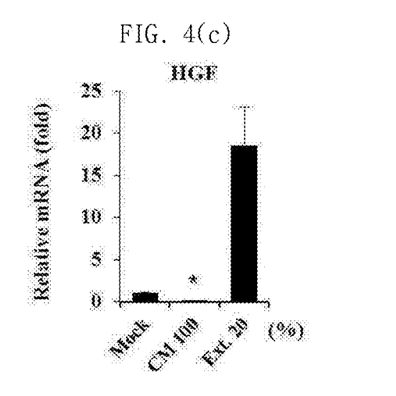
Figure 4D:
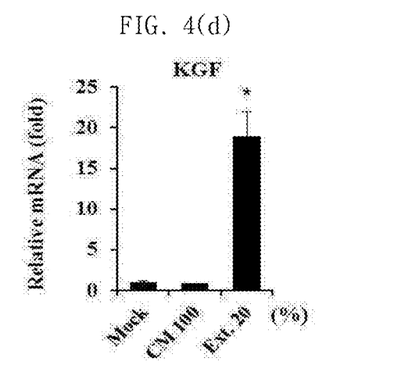
Figure 4E:
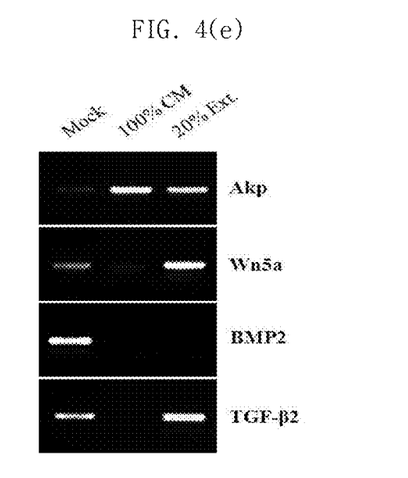

In addition, dermal papilla cells were treated with the conditioned medium of neural stem cells or the extract of neural stem cells according to the present invention, after which the proliferation of the dermal papilla cells was analyzed by a WST-1 assay at 24-hr intervals for 72 hours (FIG. 3).

It was found that the conditioned medium of neural stem cells or the extract of neural stem cells according to the present invention contains various cellular growth factors and cytokines to stimulate hair growth, and particularly, induces the secretion of various growth factors, which are involved in hair growth, in dermal Papilla cells that determine hair growth stimulation (FIGS. 4a to 4e). The hair growth factor includes one or more selected from the group consisting of a vascular endothelial growth factor (VEGF), an insulin like growth factor (IGF), a hepatocyte growth factor (HGF), and a keratinocyte growth factor (KGF).

Figure 5A:
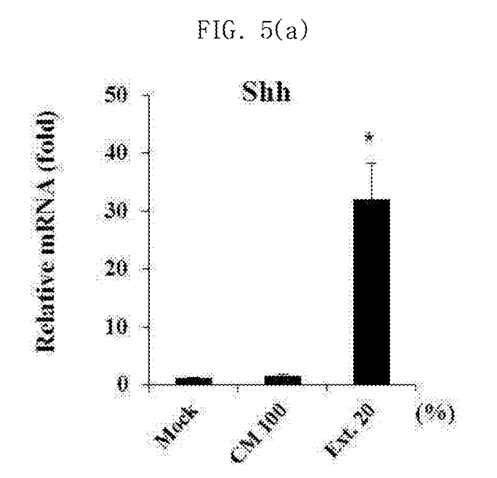
FIGS. 5a and 5b show the results of qRT-PCR, which indicate that the expression levels of leptin and the cytokine Shh (Sonic hedgehog), which induce the anagen phase of the hair cycle, were increased by each of a conditioned medium of neural stem cells and an extract of neural stem cells according to the present invention.
Figure 5B:
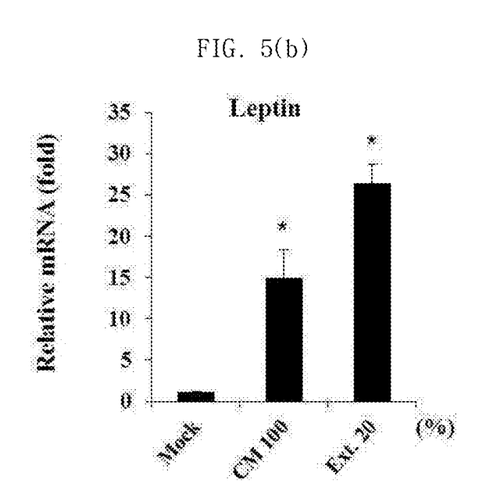

It was found that the conditioned medium of neural stem cells or the extract of neural stem cells according to the present invention contains various cellular growth factors and cytokines to stimulate hair growth, and particularly, stimulates the expression of the cytokine Shh (Sonic hedgehog) that induces the anagen phase of the hair cycle, which determines hair growth stimulation (FIGS. 5a and 5b).

Figure 6A:
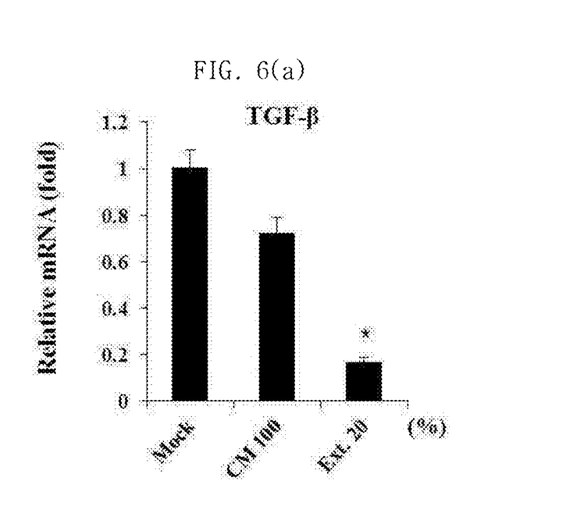
FIGS. 6a and 6b show the results of qRT-PCR, which indicate that the expression of TGF-β1 (transforming growth factor beta 1) and IL-6, which induce the catagen phase of the hair cycle, was inhibited by each of a conditioned medium of neural stem cells and an extract of neural stem cells according to the present invention.
Figure 6B:
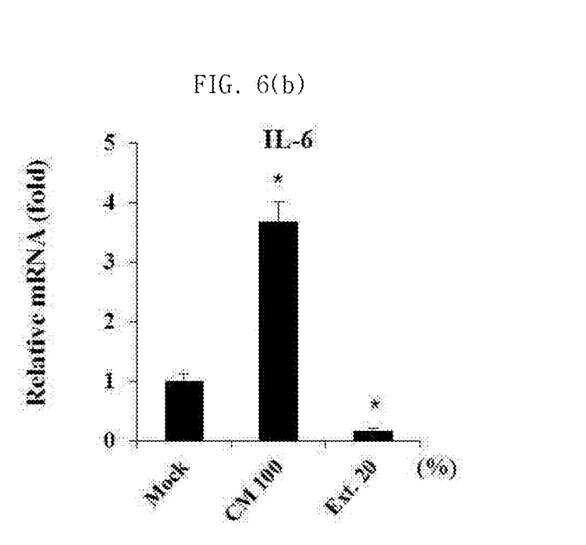

It was found that the conditioned medium of neural stem cells or the extract of neural stem cells according to the present invention inhibits the expression of TGF-β1 (transforming growth factor beta 1) that induces the catagen of the hair cycle, unlike a control (FIGS. 6a and 6b).

Figure 7A:
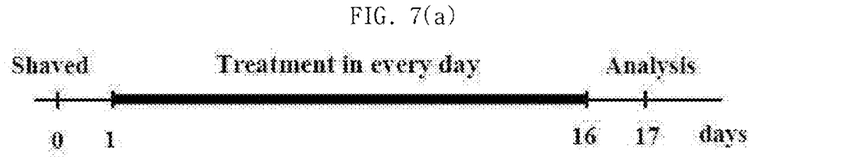
FIGS. 7a and 7b are photographs showing that the growth of hair in shaved mice was stimulated when each of a conditioned medium of neural stem cells and an extract of neural stem cells according to the present invention was applied to the shaved mice for a certain period of time.
Figure 7B:
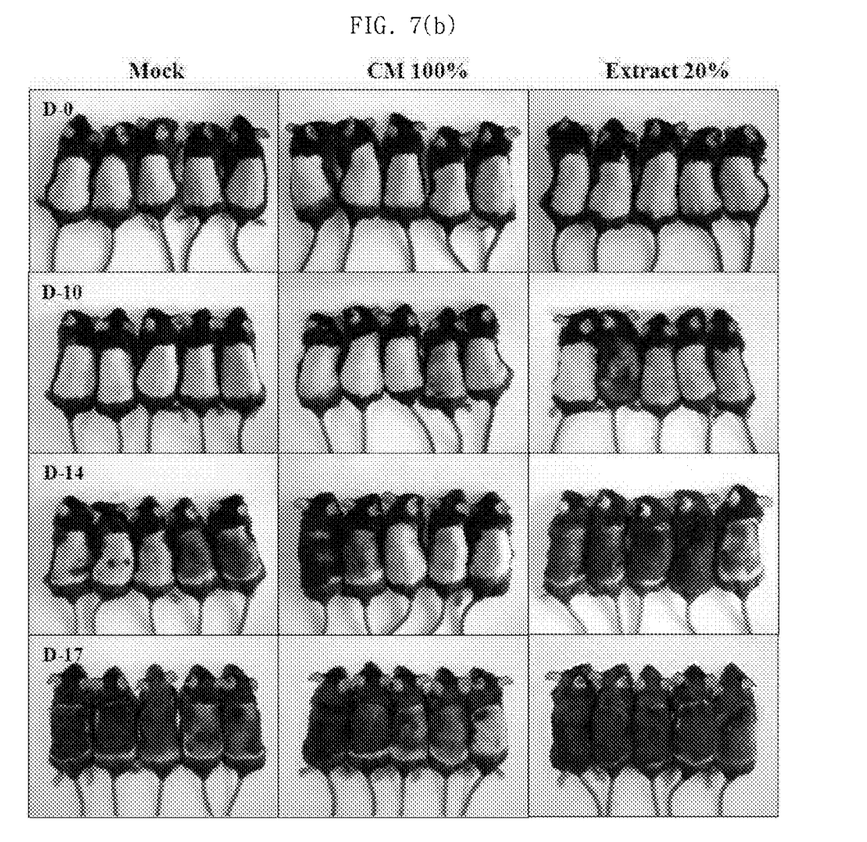

In an example of the present invention, in order to examine whether the conditioned medium of neural stem cells or the extract of neural stem cells has an activity of stimulating hair growth, the backs of shaved C57BL/6 mice were treated with varying concentrations of the conditioned medium of neural stem cells or the extract of neural stem cells. As a result, it was shown that an increase in hair growth in the group treated with the neural stem cell-conditioned medium (CM) and the group treated with the neural stem cell extract (Ext.) was induced, unlike that in the control group (Mock) (FIGS. 7a and 7b).

Figure 8A:
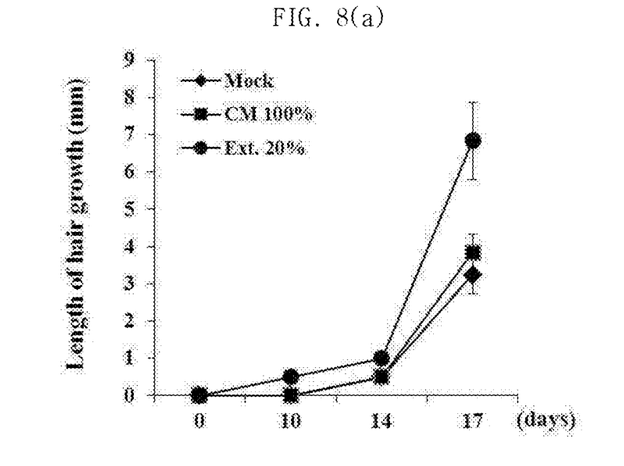
FIGS. 8a to 8c show the hair length and weight of shaved mice, which indicate that the growth of hair in the shaved mice was stimulated when each of a conditioned medium of neural stem cells and an extract of neural stem cells according to the present invention was applied to the shaved mice for a certain period of time.
Figure 8B:
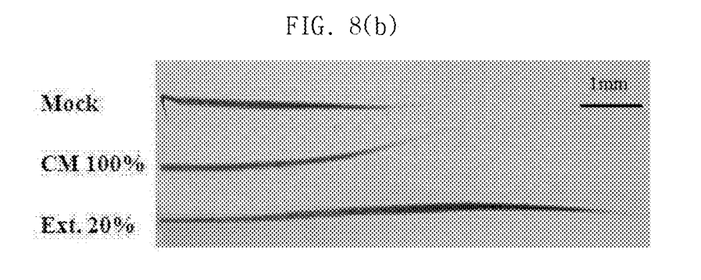
Figure 8C:
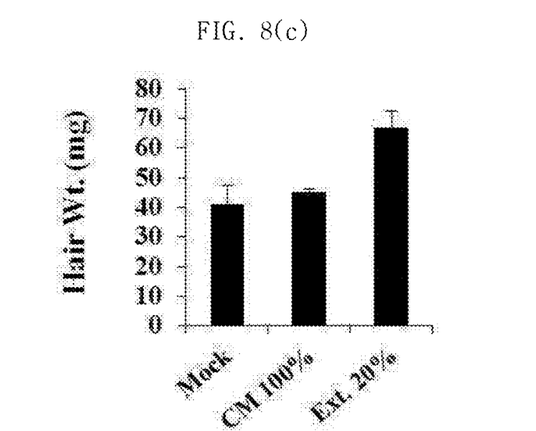

It was shown that the anagen phase of the hair cycle in the group treated with the conditioned medium of neural stem cells and the group treated with the extract of neural stem cells was induced, unlike the control group, and thus the length and weight of hair in the treated groups were also increased (FIGS. 8a to 8c).

Figure 9A:
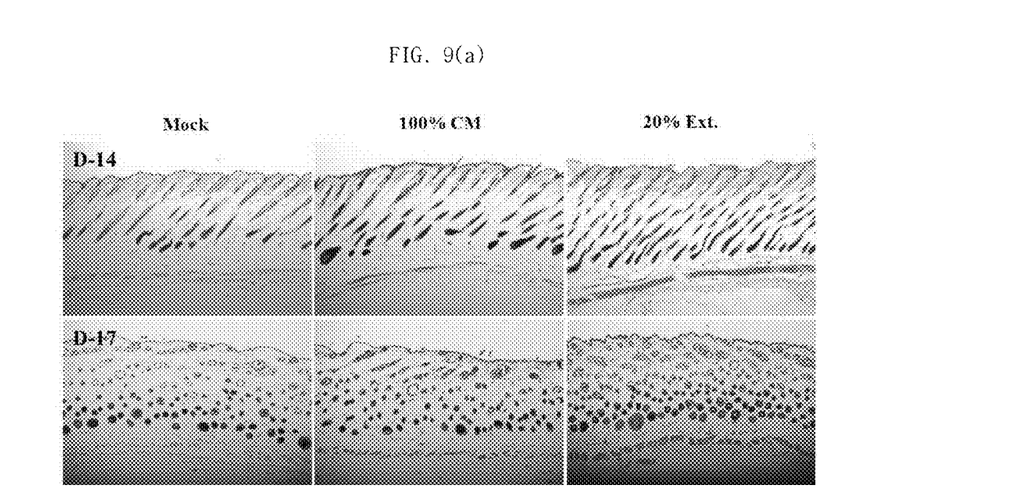
FIGS. 9a and 9b show the results of H & E (hematoxylin and eosin) staining, which indicate that the growth of hair follicles was induced after the application of each of a conditioned medium of neural stem cells and an extract of neural stem cells according to the present invention.
Figure 9B:
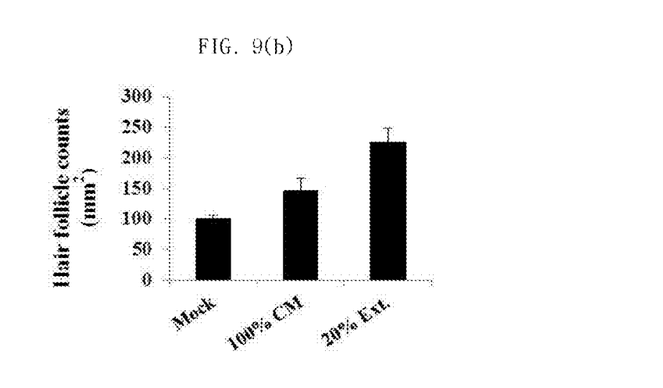

It was found that the number of hair follicles activated the same period of time was larger in the group treated with the conditioned medium of neural stem cells or the extract of neural stem cells than in the control group (FIGS. 9a and 9b).

Figure 10A:
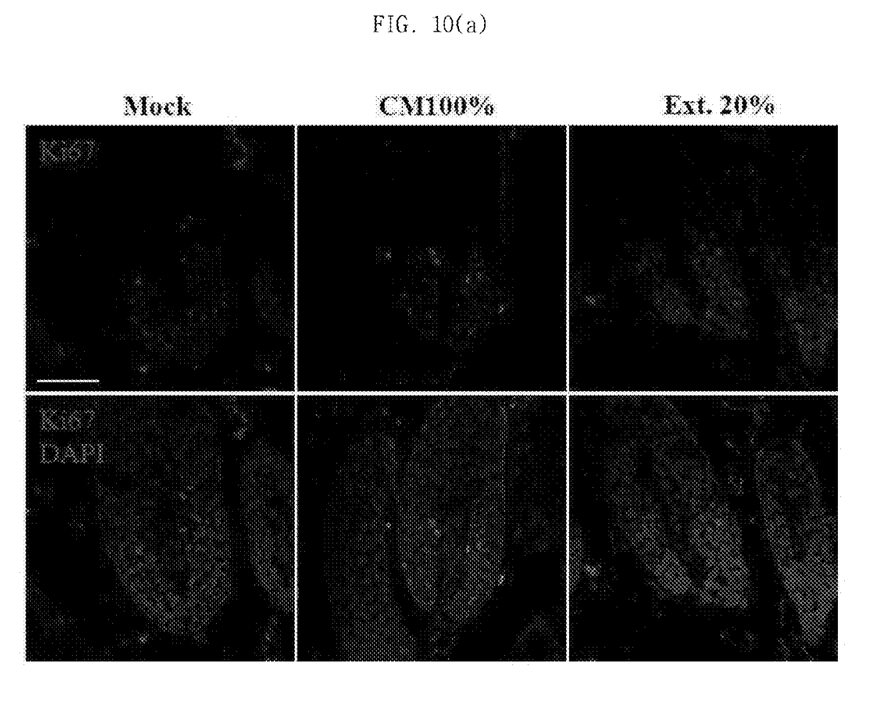
FIGS. 10a and 10b show the results of immunohistochemistry, which indicate that the growth of cells in shaved mice was increased after each of a conditioned medium of neural stem cells and an extract of neural stem cells according to the present invention was applied to the shaved mice.
Figure 10B:
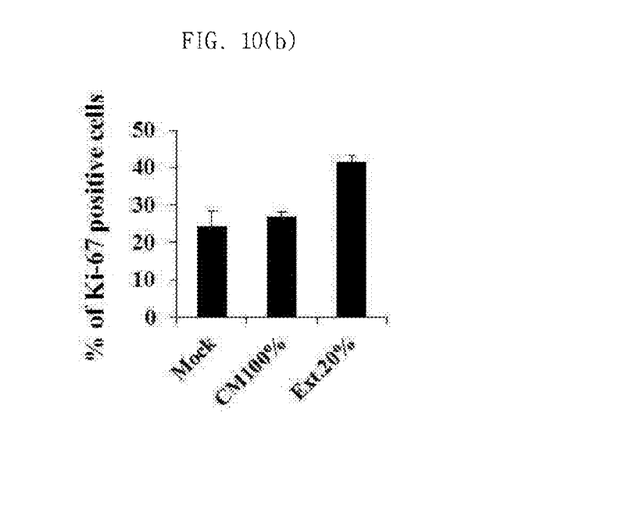

The cell proliferation marker Ki-67 in each of the control group and the group treated with the conditioned medium of neural stem cells or the extract of neural stem cells was analyzed. As a result, it was shown that, in the group treated with the conditioned medium of neural stem cells or the extract of neural stem cells, cell proliferation was activated, and cell death did not also occur (FIGS. 10a and 10b).

Figure 11:
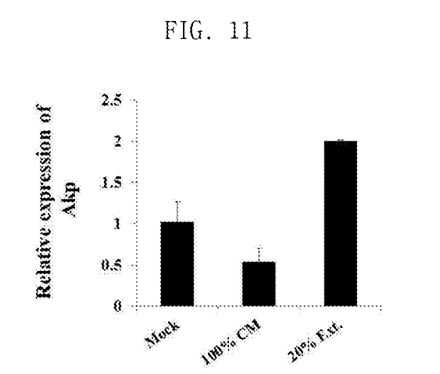
FIG. 11 shows the results of qRT-PCR, which indicate that the expression of the dermal papilla cell marker alkaline phosphatase (Akp) in the tissue of shaved mice was increased after each of a conditioned medium of neural stem cells and an extract of neural stem cells according to the present invention was applied to the shaved mice.

In addition, it was found that the expression of the dermal papilla cell marker alkaline phosphatase (Akp) mRNA in the group treated with the conditioned medium of neural stem cells or the extract of neural stem cells increased compared to that in the control group (FIG. 11).

Figure 12:
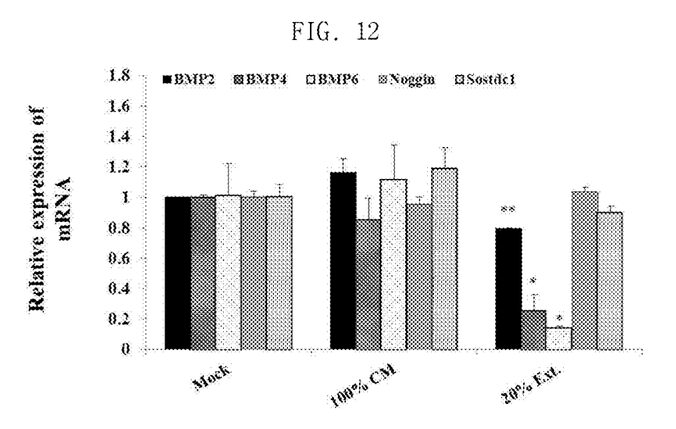
FIG. 12 shows the results of qRT-PCR, which indicate that the expression levels of the BMP family (that inhibit stem cell differentiation) in the hair follicles of shaved mice were reduced after each of a conditioned medium of neural stem cells and an extract of neural stem cells according to the present invention was applied to the shaved mice.

The expression levels of the BMP (bone morphogenetic protein) family, known to inhibit hair growth by inhibiting the differentiation of bulge stem cells, in the control group and the group treated with the conditioned medium of neural stem cells or the extract of neural stem cells, were analyzed. As a result, the expression levels of the BMP family in the group treated with the neural stem cell extract (Ext.) were reduced compared to those in the control group (Mock) and the group treated with the neural stem cell-conditioned medium (CM) (FIG. 12).

Figure 13A:
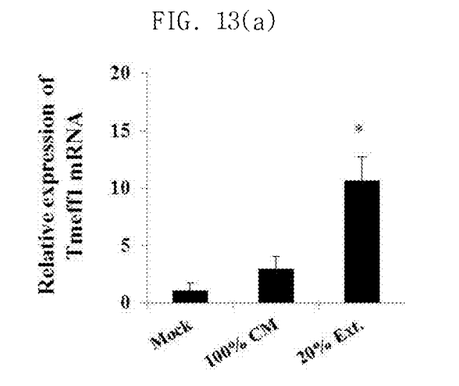
FIG. 13 shows the results of qRT-PCR, which indicate that the expression level of Tmeff1 (that inhibits the expression of BMPs) and the expression level of TGF-β2 (that increases the expression of Tmeff1) were increased after each of a conditioned medium of neural stem cells and an extract of neural stem cells according to the present invention was applied to the shaved mice.
Figure 13B:
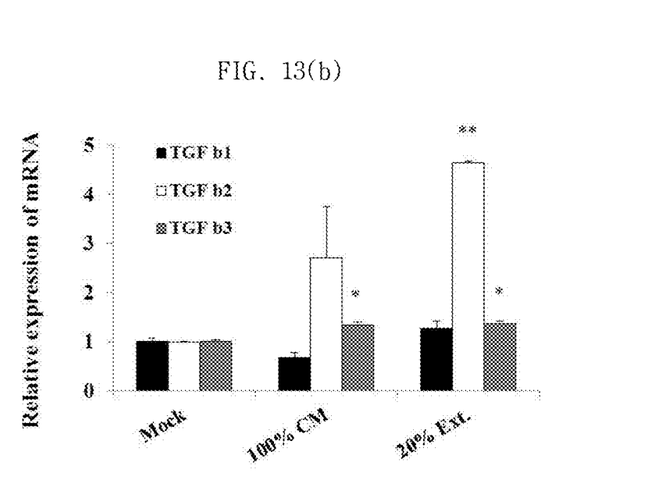

The mRNA expression levels of Tmeff1 (that inhibits the expression of BMPs) and TGF-β2 (that increases the expression of Tmeff1) in the control group and the group treated with the neural stem cell-conditioned medium or the neural stem cell extract were analyzed. As a result, it was shown that the expression levels of Tmeff1 and TGF-β2 in the group treated with the neural stem cell extract (Ext.) were increased (FIGS. 13a and 13b).

Figure 14:
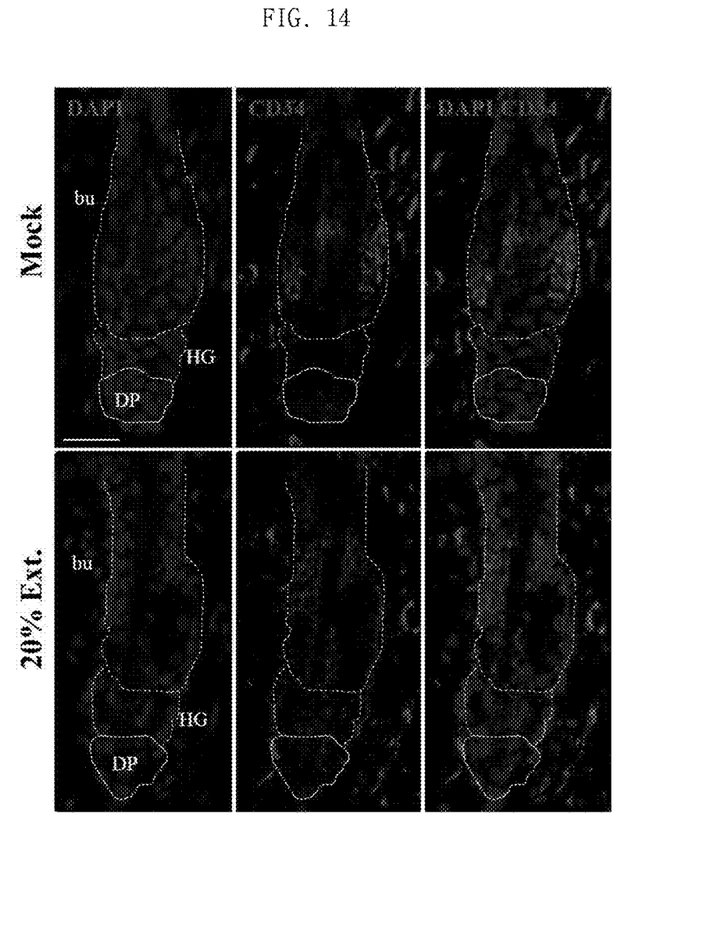
FIG. 14 shows the results of immunohistochemistry, which indicate the degree of differentiation of stem cells (CD34+) caused by a decrease in BMPs in the follicles of shaved mice after each of a conditioned medium of neural stem cells and an extract of neural stem cells according to the present invention was applied to the shaved mice.

The degrees of differentiation of stem cells (CD34+) caused by a decrease in BMPs in the control group and the group treated with the conditioned medium of neural stem cells or the extract of neural stem cells were analyzed. As a result, it was shown that stem cells in the group treated with the neural stem cell extract (Ext.) were activated (FIG. 14).

As a medium for culture of neural stem cells in the present invention, any basal medium known in the art may be used without limitation. The basal medium that is used in the present invention may be a synthetic basal medium or a commercially available basal medium. Examples of the commercially available basal medium include Dulbecco's modified eagle's medium (DMEM), minimal essential medium (MEM), basal medium eagle (BME), RPMI 1640, F-10, F-12, a-minimal essential medium (a-MEM), Glasgow's minimal essential medium (G-MEM), and Isocove's modified Dulbecco's medium, but is not limited thereto. The commercially available basal medium may be DMEM.

The basal medium preferably contains 0.01-15% (v/v) of FBS. In an example of the present invention, neural stem cells were cultured in 10% FBS-containing DMEM medium, and the effect thereof on the stimulation of hair growth was measured.

As used herein, "composition for stimulating hair growth or preventing hair loss" is a composition containing the conditioned medium of neural stem cells or the extract of neural stem cells, and may be in any formulation. Examples of the formulation of the composition for stimulating hair growth or preventing hair loss include solution, gel, cream, lotion, powder, skin lotion, foundation and solid soap. For the purpose of the present invention, the composition may be prepared and used in any of such formulations, and the formulation of the composition is not limited to the above examples. The composition for stimulating hair growth or preventing hair loss according to the present invention may contain, in addition to the above-described active ingredient, components that are generally used in compositions for stimulating hair growth or preventing hair loss, for example, conventional additives such as antioxidants, stabilizers, solubilizers, vitamins, pigments and fragrance, and carriers.

The present invention may also provide a pharmaceutical composition for stimulating hair growth or preventing hair loss, which contains the conditioned medium of neural stem cells or the extract of neural stem cells.

A pharmaceutically acceptable carrier contained in the pharmaceutical composition of the present invention is typically used in the formulation. Examples thereof include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrups, methyl cellulose, methylhydroxybenzoate, propylhydroxybenzoate, talc, magnesium stearate, and mineral oil, but are not limited thereto. The pharmaceutical composition of the present invention may further include lubricants, wetting agents, sweeteners, aromatics, emulsifiers, suspensions, and preservatives besides the above components. The pharmaceutically acceptable carriers and formulations that is suitable for the pharmaceutical composition of the present invention are in detail described in Remington's Pharmaceutical Sciences (19th ed., 1995).

The preferred dosage of the pharmaceutical composition of the present invention can be suitably selected depending on various factors, including formulation method, administration method, the patient's age, weight and gender, the severity of disease, the route and period of administration, excretory speed, and response sensitivity. A skilled doctor can easily determine and prescribe the dosage effective for the desired treatment. Meanwhile, the pharmaceutical composition of the present invention may be administered at a daily dose of from 0.01-2,000 mg/kg, but not limited thereto.

The pharmaceutical composition of the present invention can be administered orally or parenterally. In case of the parenteral administration, the pharmaceutical composition of the present invention may be administered by intravenous injection, subcutaneous injection, intramuscular injection, intraperitoneal injection, and transdermal injection. The route of administration of the pharmaceutical composition of the present invention is preferably determined depending on the type of disease to which the inventive pharmaceutical composition is applied. For example, the pharmaceutical composition of the present invention is used for the stimulation of hair growth or the prevention and treatment of hair loss, and thus is preferably administered in a manner as to be topically applied to the skin of the patient.

The pharmaceutical composition according to the present invention may be prepared in single-dose forms or in multi-dose packages using a pharmaceutically acceptable carrier and/or excipient according to a method that may be easily carried out by those skilled in the art. Herein, the formulation of the pharmaceutical composition may be a solution, suspension or emulsion of the pharmaceutical composition in oil or aqueous medium, or an extract, powder, granule, tablet or capsule containing the pharmaceutical composition, and may further comprise a dispersing agent or a stabilizer.

As used herein, the phrase "stimulating hair growth" or "preventing hair loss" is intended to include the term "hair growth" or "hair growth promotion" that is used in the art.

The composition of the present invention may be applied not only to scalp, but also to any site of the body in need of hair growth. For example, the composition of the present invention may be applied to a hair loss site resulting from a traumatic scar, or to a broad forehead or an M-shaped forehead in order to provide a simple beauty effect, and may be used to improve the conditions of atrichosis of eyelashes or eyebrows.

In another aspect, the present invention relates to a method for preparing a composition for stimulating hair growth or preventing hair loss, the method comprising the steps of: (a) culturing neural stem cells; and (b) isolating an extract of neural stem cells from a medium used to culture the neural stem cells.

The preparation of the composition may be performed by any method that is generally used in the art, and the process of isolating the extract of neural stem cells is not limited to the method of the present invention and may be performed by any method that is generally used in the art. For example, the extract of neural stem cells may be prepared by treating the cultured neural stem cells with trypsin-EDTA, subculturing the treated neural stem cells, collecting and centrifuging the medium used to culture the neural stem cells, centrifuging the supernatant, homogenizing the cell precipitate with a homogenizer, centrifuging the homogenized material, and then centrifuging the supernatant. The supernatant that is the neutral stem cell extract contains the component of the cells. In the step of isolating the neural stem cell extract, the concentration of the neural stem cell extract can be easily controlled by those skilled in the art according to a conventional extraction preparation method.

The neural stem cells that are used in step (a) are preferably cells obtained by immortalizing neural stem cells isolated from the ventricular zone of the brain, but are not limited thereto.

In step a), the neural stem cells are cultured in a medium containing 0.01-15% (v/v) FBS, but are not limited thereto. In an example of the present invention, neural stem cells (NSCs) isolated from the ventricular zone of fetal brain were immortalized to obtain cells for use in the present invention. As used herein, "immortalizing" or "immortalized" means that animal cells acquire semi-permanent proliferative activity under cell culture conditions so as to continue to proliferate without cell death. Immortalization of the cells may be performed using a technique known in the art. The immortalized cells were cultured in a non-inducible medium containing DMEM (Dulbecco's Modified Eagle's Medium), 10% FBS (fetal bovine serum) and 1% penicillin streptomycin, and non-adherent cells were removed. In the process of subculturing the neural stem cells (NSCs) cultured as described above, the conditioned medium was collected. The collected medium was centrifuged, and the supernatant was filtered. Meanwhile, an extract of the neural stem cells was obtained by homogenizing the cultured cells treated with trypsin-EDTA.

As described above, the ectodermal neural stem cell-conditioned medium or the ectodermal neural stem cell extract according to the present invention may be advantageously used as a raw material for the development of drugs (or quasi-drugs) capable of stimulating hair growth or preventing or treating hair loss.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Production of Neural Stem Cell-Conditioned Medium and Neural Stem Cell Extract Neural stem cells (NSCs) isolated from the ventricular zone of the fetal brain were immortalized to obtain cells. Specifically, 14-week-old fetal neural cell tissue was treated with a solution containing 0.1% collagenase and 0.1% hyaluronidase at 37° C. for 1 hour and treated with 0.05% Trypsin-EDTA for 2-3 minutes to isolate single cells. Then, the cells were separated by FACS using markers (CD45−/CD133+/CD34−). The separated cells were cultured in human neurosphere culture media containing N-2 supplements, 0.2 mg/ml heparin, 20 ng/ml bFGF (basic Fibroblast Growth Factors), 20 ng/ml EGF (Epidermal Growth Factor) and 10 ng/ml LIF (leukemia inhibitory factor).

After 10-14 days, the formed neurospheres were treated with collagenase to isolate single cells, and v-myc gene was transfected into the cells using a retroviral vector. Then, the cells obtained through a selection process were cultured in a non-inducible medium containing DMEM (Dulbecco's Modified Eagle's Medium), 10% FBS (fetal bovine serum) and 1% penicillin/streptomycin (Engraftable human neural stem cells respond to elvelopmental cues, replace neurons, and espress forevel genes, Flax J D et al., *Nature Biotechnology*, vol. 16, 1998; Neuroprotective effect of neural stem cell-contionee meeia in in vaxro moeel of Huntington's disease, Lim H-C et al., *Neuroscience Letters* 435, pp 175-180, 2008).

The cells were seeded into 150 mm culture dishes at a density of $5 \times 10^5$ cells, and 15 ml of culture medium was added to the cells. Then, the cells were cultured in a 5% $CO_2$ incubator at 37° C., and when the cells reached a confluence of 80%, the medium was collected. Herein, the medium was the non-inducible medium containing DMEM (Dulbecco's Modified Eagle's Medium), 10% FBS (fetal bovine serum) and 1% penicillin/streptomycin. After culture, non-adherent cells were removed. In the process of subculturing the neural stem cells (NSCs) cultured as described above, the medium was collected. The collected medium was centrifuged, and the supernatant was filtered, thereby obtaining a conditioned medium of neural stem cells. Meanwhile, to obtain an extract of neural stem cells, the cultured cells treated with Trypsin-EDTA were washed twice with PBS, added to 100 ml of triple-distilled water, homogenized with a homogenizer at 6,000 RPM for 5, and then centrifuged at 1500 rpm for 5 minutes, and the supernatant was collected.

Example 2: Total Protein Concentrations of Neutral Stem Cell-Conditioned Medium and Neural Stem Cell Extract A sample was added to a 96-well plate in an amount corresponding to a protein amount of 10-100 μg, and the total volume was adjusted to 100 μl. As a blank, 100 μl of distilled water was added to a 96-well plate. Next, the dye Coomassie blue was added to the 96-well plate, and the absorbance at 595 nm was measured using a microplate reader.

As a result, as shown in FIG. 1, the neural stem cell-conditioned medium and the neural stem cell extract had high protein concentrations.

Example 3: Measurement of Cell Viability and Proliferation of Neural Stem Cell-Conditioned Medium and Neural Stem Cell Extract $1 \times 10^3$ cells were seeded into each well of a 96-well plate. The next day, the cells were treated with 100 μl of each of the neural stem cell-conditioned medium (0-100%) and the neural stem cell extract. 10 μl of an assay (WST-1) substance was added to each well at 24-hour intervals, followed by incubation in an incubator. Next, the absorbance at 440 nm was measured using a microplate reader.

As a result, as shown in FIGS. 2a and 3, the neural stem cell-conditioned medium and the neural stem cell extract showed high cell viability and proliferation.

Example 4: Measurement of Expression Levels of Hair Growth Factors and Cytokines by Quantitative RT-PCR In this Example, dermal papilla cells were seeded into a 24-well plate at a density of $1.5 \times 10^4$ cells per well. The next day, the cells were treated with 100 μl of each of the neural stem cell-conditioned medium (0-100%) and the neural stem cell extract. At 72 hours after the treatment, the cells were washed with phosphate buffered saline (PBS), and total RNA was isolated from the cells using Trizol reagent and synthesized into cDNA using reverse transcriptase. The cDNA was subjected to quantitative RT-PCR.

As a result, as shown in FIG. 3a to FIG. 6b, in the group treated with each of the neural stem cell-conditioned medium and the neural stem cell extract, VEGF, IGF, HGF and KGF growth factors, which are involved in hair growth, and Shh that induces the anagen phase of the hair cycle, was high, were expressed at high levels, and TGF-β1 that induces the catagen phase of the hair cycle was expressed at low levels.

Example 5: Examination of Effects of Neural Stem Cell-Conditioned Medium and Neural Stem Cell Extract on Stimulation of Hair Growth in C57BL/6J Skin Tissue 5-week-old C57BL/6J mice were acclimated at 24±2° C. for 7 days, and then the back of the mice was shaved and treated once a day with 1 ml of the neural stem cell-conditioned medium (100%, v/v) or neural stem cell extract (20%, v/v) of the present invention. As a control, complete culture medium (DMEM+10% FBS) was used. After treatment with the medium or the extract, the hair on the back was observed at certain intervals. After 16 days, the effect of the medium or the extract on the stimulation of growth of hair in the mice was examined.

As a result, as shown in FIGS. 7a and 7b, the neural stem cell-conditioned medium and the neural stem cell extract (20%, v/v) showed the effect of stimulating hair growth, compared to the control.

Example 6: Analysis of Effects of Neural Stem Cell-Conditioned Medium and Neural Stem Cell Extract on Stimulation of Hair Growth in C57BL/6J Skin Tissue 1: Analysis of Hair Length and Weight 5-week-old C57BL/6J mice were acclimated at 24±2° C. for 7 days, and then the back of the mice was shaved and treated once a day with 1 ml of the neural stem cell-conditioned medium (100%, v/v) or neural stem cell extract (20%, v/v) of the present invention. As a control, complete culture medium (DMEM+10% FBS) was used. After treatment with the medium or the extract, the hair on the back was observed at certain intervals. After 16 days, the mice were sacrificed, and the hair length and weight of the mice were measured to confirm the effect of stimulating hair growth.

As a result, as shown in FIGS. 8a to 8c, the neural stem cell-conditioned medium and the neural stem cell extract (20%, v/v) had effects on the stimulation on hair growth in terms of the hair growth time and the hair length and weight. Particularly, the neural stem cell extract had a better effect.

2: H & E Staining of Tissue 5-week-old C57BL/6J mice were acclimated at 24±2° C. for 7 days, and then the back of the mice was shaved and treated once a day with 1 ml of the neural stem cell-conditioned medium (100%, v/v) or neural stem cell extract (20%, v/v) of the present invention. As a control, complete culture medium (DMEM+10% FBS) was used. After treatment with the medium or the extract, the hair on the back was observed at certain intervals. After 16 days, the mice were sacrificed, and the hair follicles were counted to confirm the effect of stimulating hair growth.

As a result, as shown in FIGS. 9a to 9b, the neural stem cell-conditioned medium and the neural stem cell extract (20%, v/v) had effects on the stimulation on hair growth in terms of the hair growth time and the hair follicle count. Particularly, the neural stem cell extract had a better effect.

3: Analysis of Cell Growth Marker 5-week-old C57BL/6J mice were acclimated at 24±2° C. for 7 days, and then the back of the mice was shaved and treated once a day with 1 ml of the neural stem cell-conditioned medium (100%, v/v) or neural stem cell extract (20%, v/v) of the present invention. As a control, complete culture medium (DMEM+10% FBS) was used. After treatment with the medium or the extract, the hair on the back was observed at certain intervals. After 16 days, the mice were sacrificed, and the skin tissue was fixed in 4% formaldehyde, embedded in paraffin, and sectioned to a thickness of 3 µm. The sections were attached to slides, deparaffinized and rehydrated. Then, the sections were subjected to antigen retrieval (citrate buffer, pH 6.0), treated with 0.1% Triton) X-100, blocked with normal donkey serum, and then treated with a 1:250 dilution of primary antibody for 24 hours. Then, the sections were treated with secondary antibody for 1 hour, and stained with DAPI for 5 minutes. Next, the sections were fixed to slides using vectashield mounting medium, and then observed with a confocal microscope.

As a result, as shown in FIGS. 10a and 10b, it was observed that the cell growth marker Ki-67 increased in the neural stem cell-conditioned medium and the neural stem cell extract (20%, v/v).

4: Analysis of Gene Expression in Tissue 5-week-old C57BL/6J mice were acclimated at 24±2° C. for 7 days, and then the back of the mice was shaved and treated once a day with 1 ml of the neural stem cell-conditioned medium (100%, v/v) or neural stem cell extract (20%, v/v) of the present invention. As a control, complete culture medium (DMEM+10% FBS) was used. After treatment with the medium or the extract, the hair on the back was observed at certain intervals. After 16 days, the mice were sacrificed, and the skin tissue was treated with Trizol reagent to isolate total RNA which was then synthesized into cDNA using reverse transcriptase. The cDNA was subjected to quantitative RT-PCR.

As a result, as shown in FIGS. 11 and 14, it was observed that, in the neural stem cell-conditioned medium and the neural stem cell extract (20%), the dermal papilla cell marker alkaline phosphatase increased, and the expression of BMPs that inhibits the differentiation of stem cells was reduced by increased Tmeff1 and TGF-β2 in the follicles, thereby activating the stem cells (CD34+).

INDUSTRIAL APPLICABILITY

As described above, the ectodermal neural stem cell-conditioned medium and ectodermal neural stem cell extract of the present invention contain various growth factors and cytokines, and thus have an excellent effect of stimulating hair growth. Particularly, the composition according to the present invention regulates the expression of various growth factors and Shh (Sonic hedgehog) related to hair growth, and thus exhibit the effect of fundamentally stimulating hair growth.

In addition, the ectodermal neural stem cell-conditioned medium and ectodermal neural stem cell extract of the present invention, or a specific factor(s) separated therefrom, can be used as a raw material for quasi-drugs related to hair growth stimulation. Thus, the present invention is highly useful in fields related to hair growth stimulation, hair loss prevention and baldness treatment.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for stimulating hair growth or preventing hair loss, the method comprising:
   treating a patient/subject in need of such treatment with a composition comprising an extract of neural stem cells, wherein the extract of neural stem cells is contained in the composition in an amount of 20% (v/v).

2. The method of claim 1, wherein the neural stem cells are isolated from the ventricular zone of the human brain.

3. The method of claim 1, wherein the extract of neural stem cells stimulates the expression of a growth factor, leptin and Shh (Sonic hedgehog) in dermal Papilla cells.

4. The method of claim 3, wherein the growth factor comprises one or more selected from the group consisting of a vascular endothelial growth factor (VEGF), an insulin like growth factor (IGF), a hepatocyte growth factor (HGF), and a keratinocyte growth factor (KGF).

5. The method of claim 1, wherein the extract of neural stem cells inhibits the expression of TGF-β1 or IL-6 in dermal Papilla cells.

6. The method of claim 1, wherein the extract of neural stem cells activates stem cells in a hair follicle.

7. The method of claim 6, wherein the activation of the stem cells is performed by the inhibition of the expression of BMP2, BMP4 or BMP6 and the increase of the expression of Tmeff1 or TGF-β2.

8. A method for preparing a composition for stimulating hair growth or preventing hair loss, the method comprising the steps of:
   (a) culturing neural stem cells that have been immortalized, by:
       (i) culturing the neural stem cells in a culture media containing N-2 supplements, heparin, basic fibroblast growth factor (bFGF), epidermal growth factor (EGF), and leukemia inhibitory factor (LIF) for 10-14 days; and then
       (ii) additionally culturing the cultured neural stem cells in a medium comprising DMEM (Dulbecco's Modified Eagle's Medium), 10% FBS (fetal bovine serum) and 1% penicillin/streptomycin;
   (b) isolating an extract of neural stem cells from the medium of step (a)(ii) used to culture the immortalized neural stem cells; and
   (c) incorporating said extract of neural stem cells in said composition for stimulating hair growth or preventing hair loss, in an amount of 20% (v/v).

9. The method of claim 8, wherein the neural stem cells in step (a) are isolated from the ventricular zone of the brain.

* * * * *